United States Patent [19]
Denman

[11] Patent Number: 4,850,484
[45] Date of Patent: Jul. 25, 1989

[54] ACCESSORY FOR LIVESTOCK INJECTION OPERATIONS

[76] Inventor: Dennis L. Denman, 3846 Violet Rd., Corpus Christi, Tex. 78410

[21] Appl. No.: 312,193

[22] Filed: Feb. 21, 1989

Related U.S. Application Data

[63] Continuation of Ser. No. 930,154, Nov. 13, 1986, abandoned.

[51] Int. Cl.⁴ .......................... B65D 81/18; B65D 1/24
[52] U.S. Cl. .................................. 206/366; 62/457.1; 62/371; 206/563; 206/571; 211/74; 220/18; 220/23; 220/23.8
[58] Field of Search ....................... 220/18, 20, 21, 23, 220/23.2, 23.4, 23.8; 206/363, 364, 365, 366, 562, 563, 570, 571; 211/74; 62/371, 457

[56] References Cited

U.S. PATENT DOCUMENTS

| | | | |
|---|---|---|---|
| 124,432 | 3/1872 | Gadsden . | |
| 2,790,547 | 4/1957 | Sutton | 206/562 |
| 3,233,804 | 2/1966 | Dahm | 211/74 |
| 3,460,899 | 8/1969 | Miller | 220/23.8 |
| 3,504,787 | 4/1970 | Brockway | 220/18 |
| 3,746,155 | 7/1973 | Seeley . | |
| 4,128,170 | 12/1978 | Ellott | 220/23 |
| 4,166,533 | 9/1979 | Maitland . | |
| 4,250,998 | 2/1981 | Taylor | 206/571 |
| 4,278,176 | 7/1981 | Adams | 211/74 |
| 4,289,238 | 9/1981 | Warncke | 220/18 |
| 4,349,338 | 9/1982 | Heppler . | |
| 4,541,539 | 9/1985 | Mathews | 220/23 |
| 4,573,973 | 4/1986 | Mezi | 206/571 |
| 4,658,957 | 4/1987 | Guth | 206/563 |

FOREIGN PATENT DOCUMENTS

| | | | |
|---|---|---|---|
| 1489929 | 4/1969 | Fed. Rep. of Germany | 211/74 |
| 986243 | 3/1965 | United Kingdom | 211/74 |
| 1116157 | 6/1968 | United Kingdom | 206/563 |

Primary Examiner—George E. Lowrance
Attorney, Agent, or Firm—G. Turner Moller

[57] ABSTRACT

An accessory for a livestock injection operation includes a multiplicity of tubular members of increasing size for temporarily holding a multiplicity of syringes during periods of nonuse. The accessory is desirably provided with a coolant to prevent overheating of the vaccines or medications. The accessory minimizes needle contamination, sunlight damage to the vaccine, injury to the operator or helper and is easy to use.

20 Claims, 2 Drawing Sheets

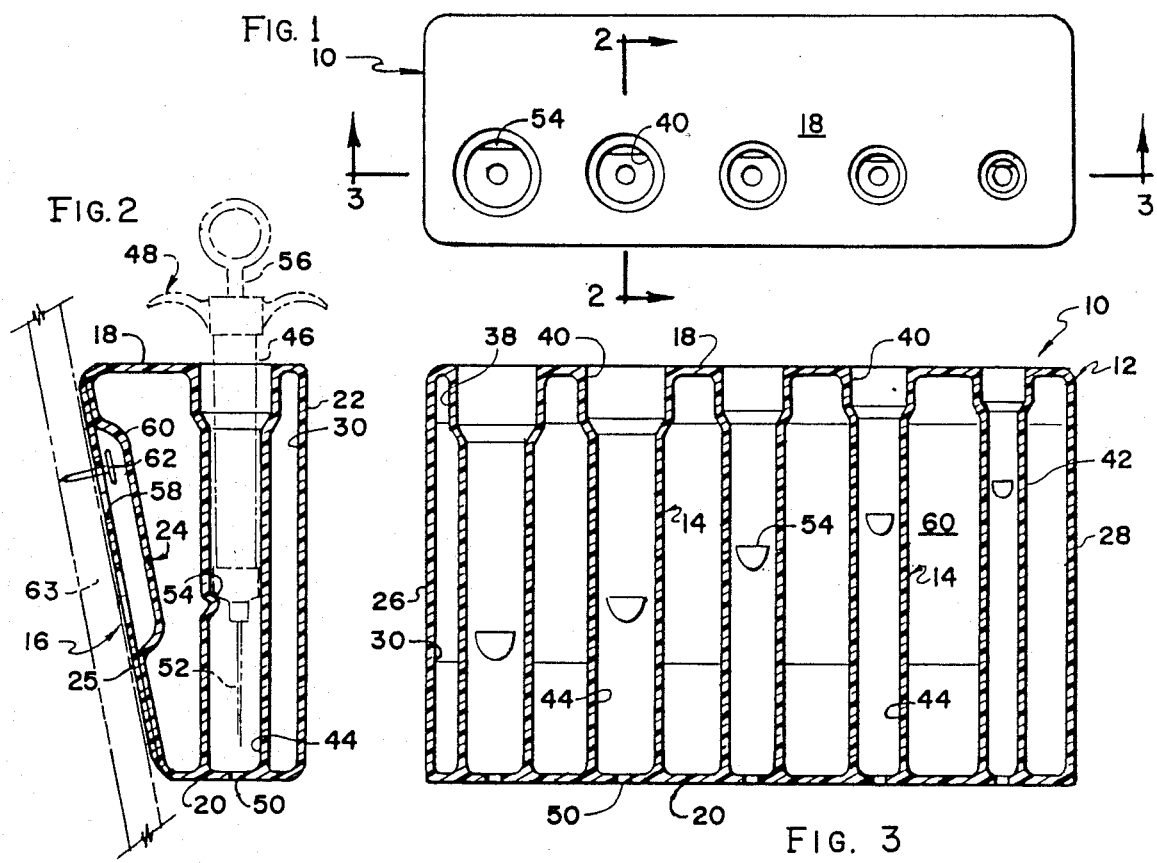
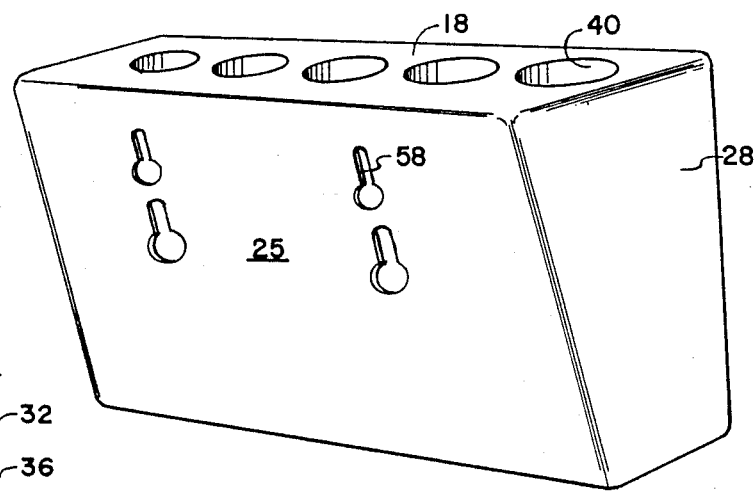
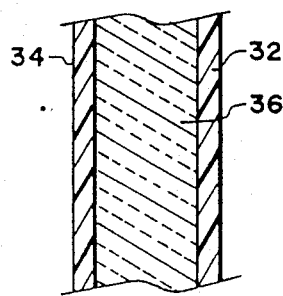

ACCESSORY FOR LIVESTOCK INJECTION OPERATIONS

This is a continuation of application Ser. No. 06/930,154, filed Nov. 13, 1986, now abandoned.

This invention relates to an accessory for a veterinarian or livestock producer to use when vaccinating livestock.

When a veterinarian or livestock producer vaccinates or medicates livestock, it is quite common to use large multiple dose syringes so that multiple animals can be treated without having to refill the syringe after every animal. Because the animals may be immunized with a number of different vaccines at the same time, three or four syringes are often used concurrently.

These syringes are normally placed on a table, pickup tail gate or similar location between injections. Thus, the medicines or vaccines, needles, and syringes are exposed to conditions that are less than ideal for proper immunization or medication of the livestock. Accidents invariably happen which compromise the integrity of the medications, the health and safety of the animals and the individual administering the medication. It does not take an overactive imagination to foresee that syringes fall off the tailgate of the pickup truck and stick in the dirt, the leg of the veterinarian or worse.

It is accordingly believed that there is a requirement for some technique to temporarily accommodate syringes during periods of nonuse during the vaccination of livestock. Preferably, the selected technique would consider the effects of temperature, sunlight, needle contamination, operator injury, convenience and physical limitations.

The thermal tolerance of vaccines or medicines is often exceeded because the operator seldom takes the trouble to return the syringe to an ice chest between animals. The effectiveness of a medication sometimes is lessened by exposure to high temperatures. Between uses, a syringe is normally exposed to direct sunlight which can reduce the effectiveness of medicines and particularly vaccines.

Most disposable needles are provided with a protective needle guard which is effective to prevent needle contamination from contact with dirt and the like. A needle guard is not always replaced between uses because of the grief involved in removing, finding and replacing it. Many reusable needles are not provided with needle guards at all.

The person injecting the livestock occasionally punctures himself during removal of the needle guard, trying to protect the needle against accidental contamination and the like. Occasionally, helpers get poked with the needle while the operator is picking the syringe up, putting it down and the like. Besides being aggravating, this can be serious business when using modified live vaccines such as Brucella Strain 19. It is bad policy to inoculate humans with such vaccines.

Because livestock injections normally occur in the field, there is often not available a convenient spot to place the syringes between uses. Almost invariably, the closest place is several steps away. In addition, working livestock can be like a Chinese fire drill because the person giving the injections has a lot of other things to do. For example, the veterinarian may be pregnancy checking cows and have a obstetrical sleeve on one arm and hand thereby leaving only one hand free to vaccinate the cow.

Preferably, the accessory of this invention alleviates the above problems and comprises a simple, easy to use syringe holder which protects the medication or vaccine from temperature extremes, sunlight and accidental contamination, and which minimizes the possibility of injury to the operator and helpers.

Disclosures of some interest relative to this invention are found in U.S. Pat. Nos. 124,432; 3,504,787; 3,746,155; 4,250,998; 4,166,533; and 4,349,338.

In summary, this invention comprises a livestock injection accessory for temporarily holding a plurality of syringes of the type including a barrel, comprising a frame including a plurality of generally upright tubular members having passages therein of different size from a first small cross-sectional passage to a final large cross-sectional passage, the tubular members each including an open top and a section for receiving the syringe barrel merging with the open top. Means are provided inside the section for abutting and supporting the syringe barrel, the abutting and supporting means being located in the section at a distance from the open top in proportion to the passage size of the cross-sectional member, the abutting and supporting means in the first small cross-sectional passage being closest to the open top and the abutting and supporting means in the final large cross-sectional passage being furthest from the open top. The open top of the passage is preferably larger than the lower portion thereof so the syringe is easy to replace.

It is accordingly an object of this invention to provide an accessory for livestock injections, and method of using the same, which improves efficiency of the injection process.

Another object of this invention is to provide a simple and easy to use livestock injection accessory which protects the syringes against contamination and which protects the medication or vaccine from damage due to excessive temperatures or sunlight.

Other objects and advantages of this invention will become more fully apparent as this description proceeds, reference being made to the accompanying drawings and appended claims.

IN THE DRAWINGS

FIG. 1 is a top plan view of one embodiment of this invention;

FIG. 2 is a vertical cross-sectional view of the accessory of FIG. 1, taken substantially along line 2—2 of FIG. 1 as viewed in the direction indicated by the arrows;

FIG. 3 is another vertical cross-sectional view of the accessory of FIG. 1, taken substantially along line 3—3 of FIG. 1 as viewed in the direction indicated by the arrows;

FIG. 4 is an isometric view of the embodiment of FIGS. 1-3, as viewed from the rear thereof;

FIG. 5 is a partial cross-sectional view of another embodiment of this invention;

Figure 6:
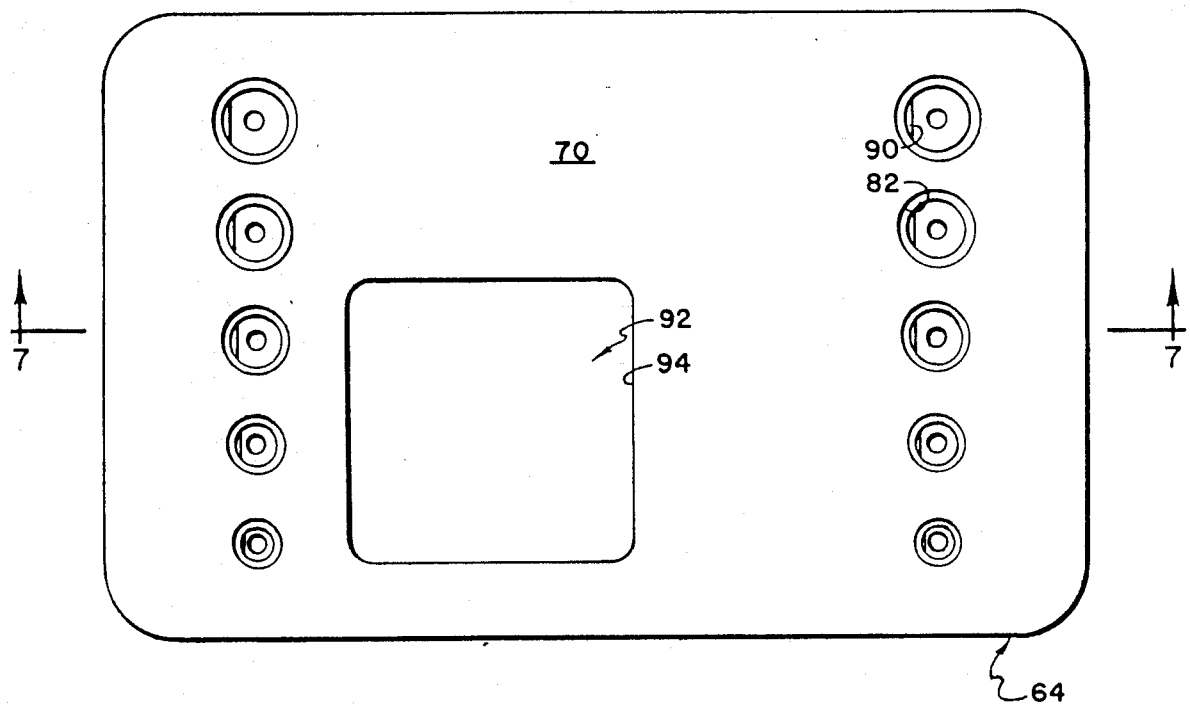
FIG. 6 is a top plan view of a further embodiment of this invention.

Referring to FIGS. 1-4, there is illustrated a livestock injection accessory 10 of this invention comprising, as major components, a frame 12, a plurality of tubular members 14 carried by the frame 12 and means 16 mounting the frame 12 on a support convenient to the injection operation.

The frame 12 comprises a top wall 18, a bottom wall 20, a front wall 22, a pair of back walls 24, 25 and a pair of end walls 26, 28 defining a compartment 30 which is illustrated as being of generally trapezoidal configuration, but which may be of any suitable shape, such as other regular rectilinear polygons. The walls of the frame 12 are conveniently made of organic polymeric material and may have insulating qualities if desired, as shown in the embodiment of FIG. 5, where inner and outer walls 32, 34 captivate an insulating material 36, such as a foamed organic polymer.

The tubular members 14 are inside the compartment 30 and, from right to left in FIG. 1, are of progressively increasing cross-sectional size providing longitudinal passages of progressively increasing diameter. The tubular members 14 each comprise an upper section 38 having a passage 40 opening through the top wall 18 and a much longer lower section 42. The lower sections 42 progressively increase in size from right to left in FIG. 1 as do the passages 44 therethrough. Preferably, the passages 44 are only slightly larger than the diameter of the barrel 46 of the syringe 48 received therein.

As is apparent, the passages 40 are considerably larger than the passages 44 thereby making it easier to replace the syringe 48 in its tubular member 14. The upper sections 38 of the tubular members 14 preferably increase in length in proportion to the diameter of the passage 44 associated therewith and accordingly increase in length in proportion to the size of the syringe 48 received in the passage 44.

The tubular members 14 preferably span between and interconnect the top wall 18 and the bottom wall 20 thereby providing rigidity to the accessory 10. The lower ends of the tubular members 14 communicate with the exterior of the frame 12 through openings or passages 50 in the bottom wall 20 thereby allowing any drippage from the syringe needle 52 to fall out of the accessory 10 and not accumulate in the bottom of the tubular members 14.

Inside each of the passages 44 is a shoulder or indentation 54 comprising means for abutting and supporting the lower end of the syringe barrel 46 at a location which preferably elevates the bottom of the needle 52 above the bottom wall 20 and which positions the syringe plunger or pistol grip 56, depending on the type of syringe, at a convenient location above the top wall 18. Because syringes tend to be longer as they are of larger diameter, the shoulders 54 are progressively located inside the passages 44 depending on the diameter thereof. As is apparent, the shoulders 54 are positioned in the passages 44 in proportion to the diameter of the passages 44 with the shoulder 54 in the smallest passage 44 being nearest the top wall 18. Thus, the top of the plungers 56 are located a convenient distance above the top wall 18 of the frame 12.

The mounting means 16 may be of any suitable type to support the accessory 10 on a support convenient to the injecting operation. Desirably, the accessory 10 is mounted on an upright wall of a chute (not shown) used to immobilize the animal during the injection. To this end, the back of the frame 12 includes a series of keyhole slots 58 in the back wall 25 with the back wall 24 including an offset portion 60 inside the compartment 30 providing a recess to receive a nail or screw head 62 in the keyhole slots 58. Conveniently, the lower keyhole slots 58 may be larger than the upper keyhole slots to receive different sized fastener heads. Thus, the inner back wall 24 captivates the coolant gel in the compartment 30 and prevents damage thereto from the nail head 62. The outer back wall 25 may be secured to the frame 12 as by adhesive, thermal or sonic bonding.

The compartment 30 is preferably filled with a heat adsorption material such as a coolant gel of any suitable description, such as the one contained in a product known as Polar-Pack manufactured by Mid-Lands Chemical Company, Inc. of Omaha, Nebr. This allows the operator to place the accessory in the freezer compartment of a refrigerator to remove heat from the coolant gel so the gel can, in turn, keep any medication or vaccine in the syringes 48 relatively cool during the injection process.

Use of the accessory 10 of this invention should now be apparent. When a veterinarian or livestock producer is preparing to inject cattle, for example, suitable fasteners are inserted in an upright wall 63 of the chute used to immobilize the animal. The keyhole slots 58 are passed over the fastener heads 62 to support the accessory on the upright wall 63. The syringes 48 are filled with the liquid material and placed, in accordance with the size thereof, in the tubular members 14.

After a first animal is immobilized in the chute, the operator retrieves a first of the syringes 48, injects the animal and returns the syringe 48 to its tubular member 14. In the event multiple injections are being given, the operator retrieves another of the syringes 48, injects the animal and then returns the syringe to its tubular member 14. After the first animal is released and a second animal immobilized in the chute, the operator sequentially injects the animal with the medications or vaccines in the syringes 48 and replaces them in their respective tubular member.

Figure 7:
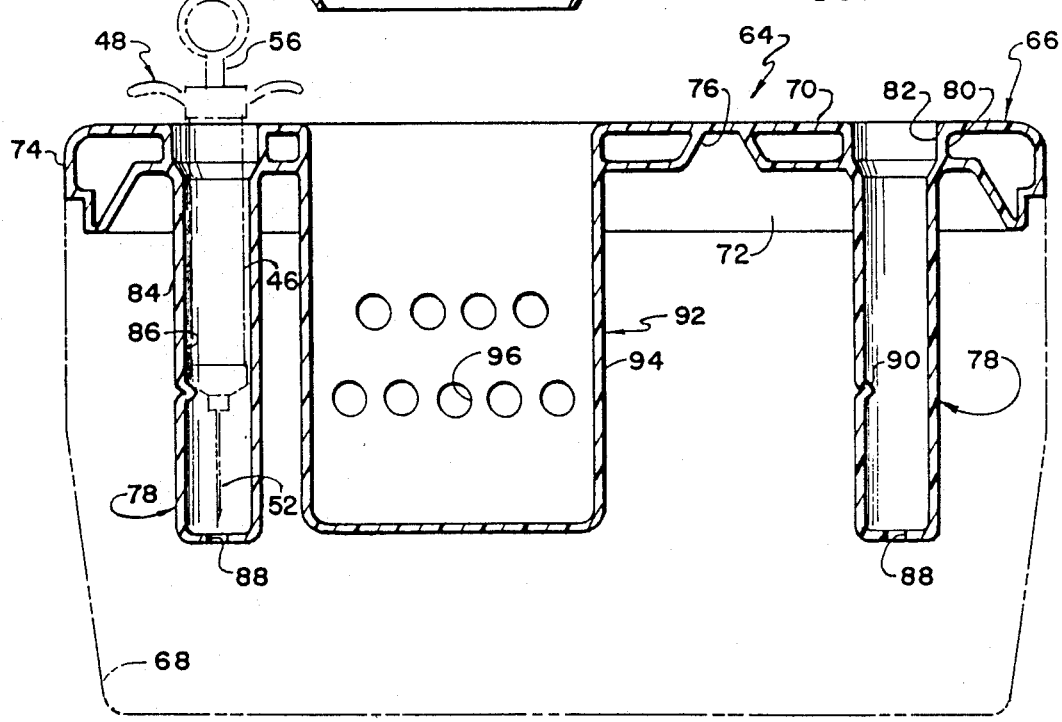
FIG. 7 is a vertical cross-sectional view of the embodiment of FIG. 6, taken substantially along line 7—7 thereof as viewed in the direction indicated by the arrows.

Referring to FIGS. 6 and 7, there is illustrated another embodiment or accessory 64 for use when injecting livestock or the like. The accessory 64 is incorporated in a lid 66 of an otherwise more-or-less conventional ice chest having a bottom container section 68. The lid 66 is sufficient to close the top of the container section 68 and is removable relative thereto, either by the use of suitable hinges (not shown) or by merely snuggly fitting in the open top of the container section 68.

The accessory 64 includes a top wall 70, a bottom wall 72, and a peripheral wall 74 providing the lid 66 with a certain thickness. Suitable gussets or ribs 76 extend across the lid 66 providing rigidity thereto as is conventional in ice chests.

A series of tubular members 78 open through the top wall 70 and extend through the bottom wall 72 into a compartment provided by the container section 68. The tubular members 78 are the same as the tubular members 14 in the embodiment of FIGS. 1-4. The tubular members 78 accordingly each comprise an upper section 80 having a passage 82 opening through the top wall 70 and a much longer lower section 84. The lower sections 84 progressively increase in cross-sectional size, or diameter, from bottom to top in FIG. 6 as do the passages 86 therethrough.

Preferably, the passages 86 are only slightly larger than the diameter of the barrel 46 of the syringe 48 received therein. As is apparent, the passages 82 are considerably larger than the passages 86 thereby making it easier to replace the syringe 48 in its tubular member 78. Like the embodiment of FIGS. 1-4, the upper sections 80 of the tubular members 78 progressively increase in length in proportion to the diameter of the passage 86 associated therewith.

The tubular members 78 extend into the cavity provided by the container section 68 and have openings or passages 88 in the bottom thereof allowing any drippage from the syringe needle 52 to fall into the container section 68 and not accumulate in the bottom of the tubular members 78.

Inside each of the passages 86 is a shoulder or indentation 90 comprising means for abutting and supporting the lower end of the syringe barrel 46 at a location which preferably elevates the bottom of the needle 52 above the bottom of the tubular member 78 and which positions the syringe plunger 56 at a convenient location above the top wall 70. Because syringes tend to be longer as they are of larger diameter, the shoulders 90 are progressively located inside the passages 86 depending on the diameter thereof, as in the embodiment of FIGS. 1-4. As is apparent, the shoulders 90 are positioned in the passages 86 in proportion to the diameter of the passages 86 with the shoulder 90 in the smallest passage 86 being nearest the top wall 70. Thus, the top of the plungers 56 are located a convenient distance above the top wall 70 of the lid 66.

The accessory 64 also includes a vaccine or medication well 92 extending into the cavity of the container section 68. The well 92 includes a container section 94 for receiving vials or containers of medication or vaccine. The container section 94 includes openings 96 therein allowing ready heat exchange with ice, dry ice, cold water or other heat absorbent material in the container section 68 of the ice chest. A suitable lid 98 for the vaccine well 92 is also provided.

In use, the accessory 64 differs from the accessory 10 in only minor respects. Because of the size of the ice chest container section 68, it is evident that a separate mounting means, analogous to the keyhole slots 58 is not necessary, because the container section 68 merely sits on the ground near the immobilizing chute. When the container section 68 is filled with ice, there is sufficient cooling capacity to keep the vaccine in the well 92 as well as the vaccine in the syringes 48 cool for prolonged periods.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A livestock injection accessory for temporarily holding a plurality of syringes of the type including a barrel, comprising
    a frame including a plurality of generally upright tubular members having passages therein of different size from a first small cross-sectional passage to a final large cross-sectional passage,
    the tubular members each including an open top, an open bottom, a section for receiving the syringe barrel merging with the open top and means for abutting and supporting the syringe barrel, the abutting and support means being located in the section at a distance from the open top in proportion to the cross-sectional size of the passage through the tubular member, the abutting and supporting means in the first small cross-sectional passage being closest to the open top and the abutting and supporting means in the final large cross-sectional passage being further from the open top.

2. The accessory of claim 1 wherein each passage includes an upper section of first cross-sectional area and a lower section of second cross-sectional area less than the first area, the first area having a length along a longitudinal axis of the passage substantially less than the length of the second area.

3. The accessory of claim 2 wherein the length of the upper sections increase in proportion to the size of the lower section passage.

4. The accessory of claim 1 wherein the frame further comprises a compartment about the tubular members for receiving a heat absorption material therein, the compartment being in liquid collecting relation to the open bottom of the tubular members.

5. The accessory of claim 4 wherein the tubular members are arranged in a linear path on the frame and the passages therein increase progressively in size from the first passage to the final passage.

6. The accessory of claim 4 further comprising a heat absorption material in the compartment.

7. The accessory of claim 4 wherein the frame comprises means for supporting the frame on an adjacent upright wall.

8. The accessory of claim 1 wherein the frame comprises front and back walls, a bottom wall, a top wall and a pair of ends walls providing a compartment, the tubular members extending from the top wall to the bottom wall, the volume between the walls and the tubular members being substantially filled with the heat absorption material, the open bottom of the tubular members comprising openings in the bottom wall.

9. The accessory of claim 4 wherein the tubular member comprises an internal wall defining the passage, the abutting and supporting means comprising a dimple in the internal wall extending into the passage.

10. The accessory of claim 4 wherein the passages are generally cylindrical and the abutting and supporting means comprises a shoulder in the passage providing a non-cylindrical passage section thereat.

11. The accessory of claim 4 wherein each passage comprises an upper section of first cross-sectional area and a lower section of second cross-sectional area less than the first area.

12. The accessory of claim 4 comprising an ice chest having a lower container section and a lid, the accessory being incorporated in the lid.

13. The accessory of claim 12 further comprising a vaccine well having a perforate wall opening through the lid and extending into the lower container section and a lid for the well opening.

14. The accessory of claim 4 wherein each passage includes an upper section of first cross-sectional area and a lower section of second cross-sectional area less than the first area, the first area having a length along a longitudinal axis of the passage substantially less than the length of the second area.

15. The accessory of claim 14 wherein the length of the upper sections increase in proportions to the size of the lower section.

16. The accessory of claim 4 wherein the abutting and supporting means being located in the section at a distance from the open top in proportion to the passage size of the cross-sectional member, the abutting and supporting means in the first small cross-sectional passage being closest to the open top and the abutting and supporting means in the final large cross-sectional passage being furthest from the open top.

17. The accessory of claim 1 further comprising a syringe having a barrel including a liquid therein and a needle connected to the barrel, the syringe being in the passage of a first of the tubular members, some of the liquid having seeped from the needle and being in the open bottom of the first tubular member.

18. A livestock injection accessory for temporarily holding a plurality of syringes of the type including a barrel, comprising a frame including a front wall, a back wall, a top and a bottom wall joining the front and back walls, means on the back wall for attaching the frame to a support and a plurality of generally upright tubular members having passages therein of different size from a first small cross-sectional passage to a final large cross-sectional passage, the passages opening through the top wall, the tubular members each including an open top, an open bottom opening through the bottom wall, a section for receiving the syringe barrel merging with the open top and means for abutting and supporting the syringe barrel, the abutting and support means being located in the section at a distance from the open top in proportion to the cross-sectional size of the passage through the tubular member, the abutting and supporting means in the first small cross-sectional passage being closest to the open top and the abutting and supporting means in the final large cross-sectional passage being further from the open top.

19. A livestock injection accessory for temporarily holding a plurality of syringes of the type including a barrel, comprising an ice chest comprising a compartment having an open top and a lid closing the open top, the lid providing a top wall, a bottom wall and a plurality of generally upright tubular members having passages therein of different size from a first small cross-sectional passage to a final large cross-sectional passage, the tubular members each including an open top opening through the top wall, a tubular section extending through the bottom wall into the compartment and having an open bottom for receiving the syringe barrel and merging with the open top and means for abutting and supporting the syringe barrel, and a well having a peripheral wall opening through the top lid wall and extending into the compartment, and a bottom wall for supporting a vaccine container therein, and a well lid closing the peripheral wall opening.

20. The livestock injection accessory of claim 19 wherein the abutting and support means is located in the section at a distance from the open top in proportion to the cross-sectional size of the passage through the tubular member, the abutting and supporting means in the first small cross-sectional passage being closest to the open top and the abutting and supporting means in the final large cross-sectional passage being furthest from the open top.

* * * * *